US00PP36344P2

(12) United States Plant Patent
Bourne

(10) Patent No.: US PP36,344 P2
(45) Date of Patent: Dec. 31, 2024

(54) GRAPEVINE PLANT NAMED 'SV36-61-150'

(50) Latin Name: ***Vitis vinifera* L.**
Varietal Denomination: SV36-61-150

(71) Applicant: Sunview Vineyards of California, Inc., Delano, CA (US)

(72) Inventor: Timothy F. Bourne, Visalia, CA (US)

(73) Assignee: Sunview Vineyard of California, Inc., Delano, CA (US)

( * ) Notice: Subject to any disclaimer, the term of this patent is extended or adjusted under 35 U.S.C. 154(b) by 0 days.

(21) Appl. No.: 18/831,058

(22) Filed: May 23, 2024

Related U.S. Application Data

(60) Provisional application No. 63/577,997, filed on Jun. 8, 2023.

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./205, 207
CPC ..... A01H 5/0812
See application file for complete search history.

*Primary Examiner* — Kent L Bell
(74) *Attorney, Agent, or Firm* — Eric C. Cole; Baker Manock & Jensen, PC

(57) ABSTRACT

A new and distinct variety of grapevine plant named 'SV36-61-150' particularly characterized by its medium, very crisp, white skinned berries with distinct fruity, non-muscat flavor and which ripen in mid August in the McFarland, California area.

5 Drawing Sheets

Latin name of the genus and species of the plant claimed: The plant claimed relates to a new and distinct variety of *Vitis vinifera* L.

Variety denomination: The plant claimed shall be known as 'SV36-61-150'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV36-61-150'. As used herein, 'grapevine' refers to all plant parts including, vines, canes, tendrils, leaves, fruit and roots of 'SV36-61-150'. Grapevine named 'SV36-61-150' is the result of an effort to produce a grapevine bearing fruit which has strong flavor with very crisp texture. This new cultivar originated from a cross conducted in May 2015 near McFarland, California between seeded, female parent grapevine selection 'SV15-68-233' (unpatented) and male parent grapevine cultivar 'SV30-27-602' (U.S. Plant Pat. No. 33,407). Resultant seeds from this cross were harvested in September of 2015 and were stratified in a refrigerator at 1° C. for 3 months. The seeds were then sown in a greenhouse at 29° C. The seedlings from this effort were grown in the greenhouse at 29° C. with 12 hours illumination under high pressure sodium vapor lamps. The seedling population of 67 plants was planted in the field in the spring of 2016 near Delano, California. The new grapevine was selected from this seedling population on Aug. 7, 2017. It was then propagated by cuttings and grafted to 'Freedom' (unpatented) rootstock in 2018. The present invention has been found to retain its distinctive characteristics through two successive asexual propagations near Delano, California in 2018 and 2022.

Grapevine named 'SV36-61-150' differs from its female parent grapevine 'SV15-68-233' (unpatented) in that 'SV36-61-150' has seedless fruit with very small seed traces while 'SV15-68-233' has berries with hard-coated seeds.

Grapevine named 'SV36-61-150' differs from its male parent grapevine 'SV30-27-602' (U.S. Plant Pat. No. 33,407) in that 'SV36-61-150' has berries with white skin while 'SV30-27-602' has berries with red skin. Grapevine named 'SV36-61-150' also differs from its male parent grapevine 'SV30-27-602 (U.S. Plant Pat. No. 33,407) in that 'SV36-61-150' has berries with a distinct fruity flavor while 'SV30-27-602' has berries with a strong muscat flavor.

Grapevine named 'SV36-61-150' most closely resembles grapevine named 'SV22-88e-124' (U.S. Plant Pat. No. 31,992) which also has white skinned berries which are very crisp. However, grapevine named 'SV36-61-150' has medium sized berries with a very distinct fruity, non-muscat flavor while grapevine named 'SV22-88e-124' (U.S. Plant Pat. No. 31,992) has small sized berries with a flavor similar to spun sugar.

SUMMARY OF THE INVENTION

The following are the most outstanding and distinguishing characteristics of the ripe fruit of this new variety when grown under normal horticultural practices near McFarland, California:

a. Medium sized berries with a strong, fruity flavor.
b. Very crisp berry texture; and
c. Medium sized clusters.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from a plant about 5 years old, grown in a field near McFarland, California in 2017, 2021 and 2022.

DETAILED BOTANICAL DESCRIPTION

Figure 1:
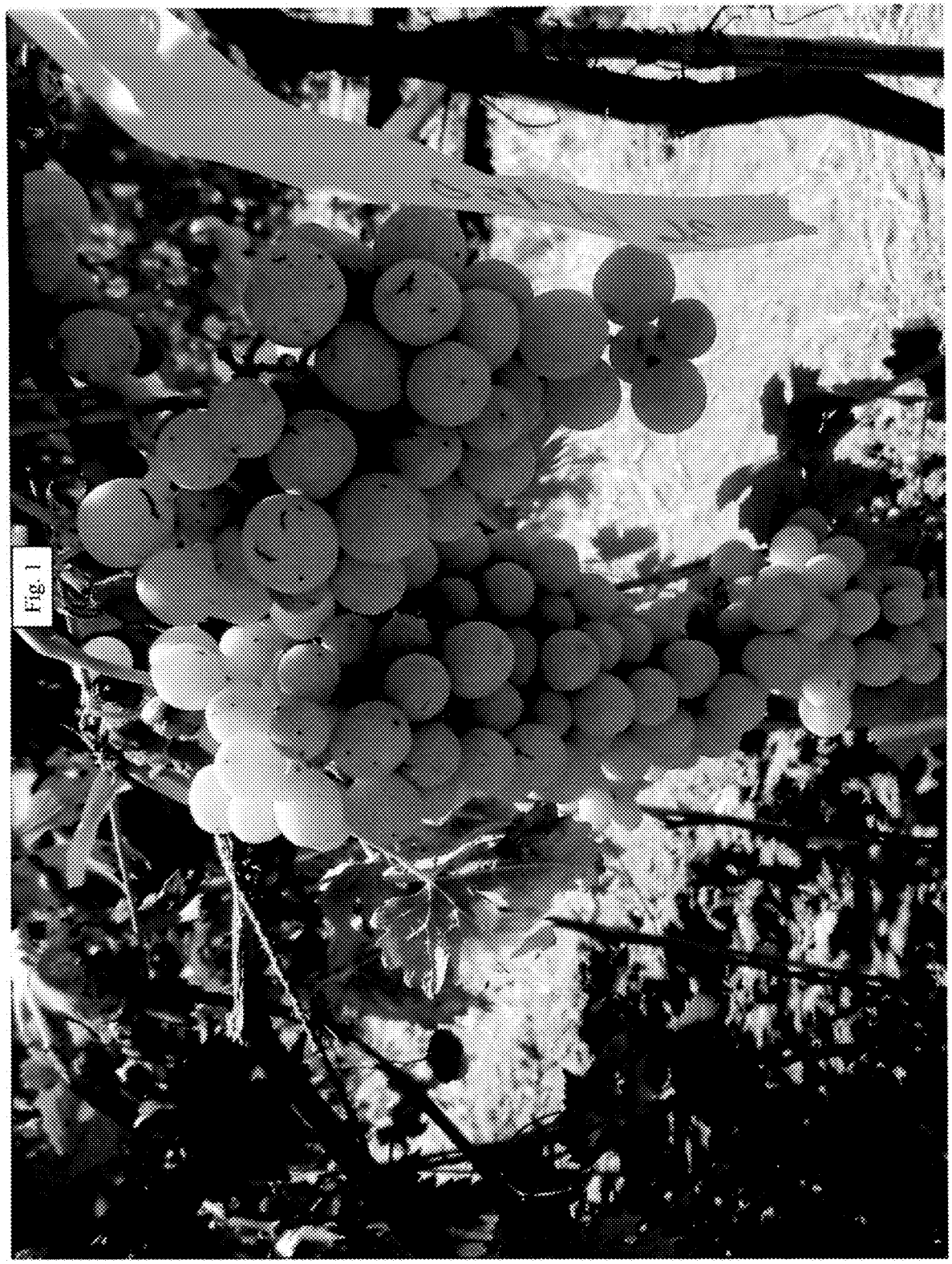
FIG. 1 Seedling vine with fruit clusters.
Figure 2:
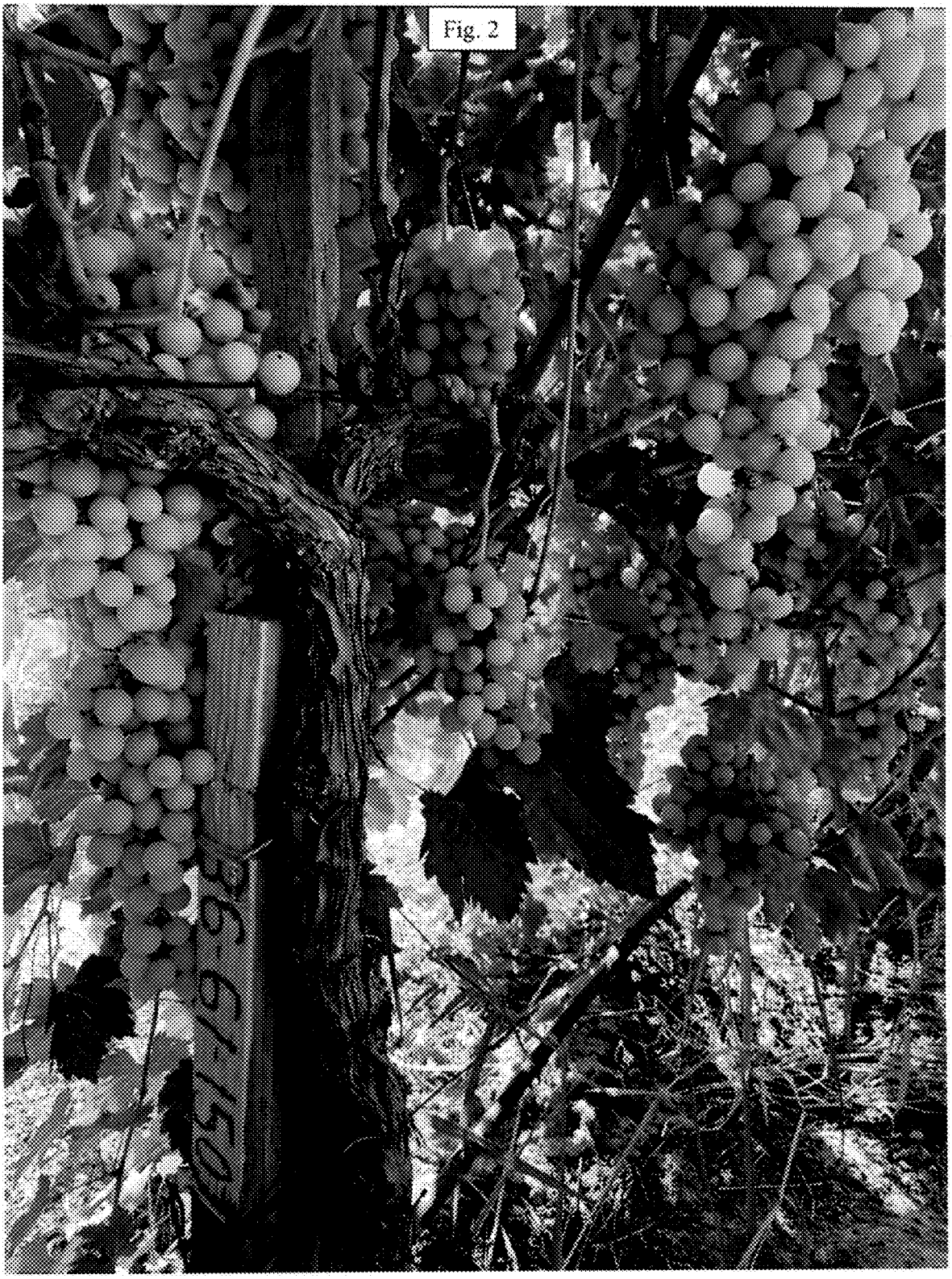
FIG. 2 Vine propagated on 'Freedom' (unpatented) rootstock with ripe fruit.
Figure 3:
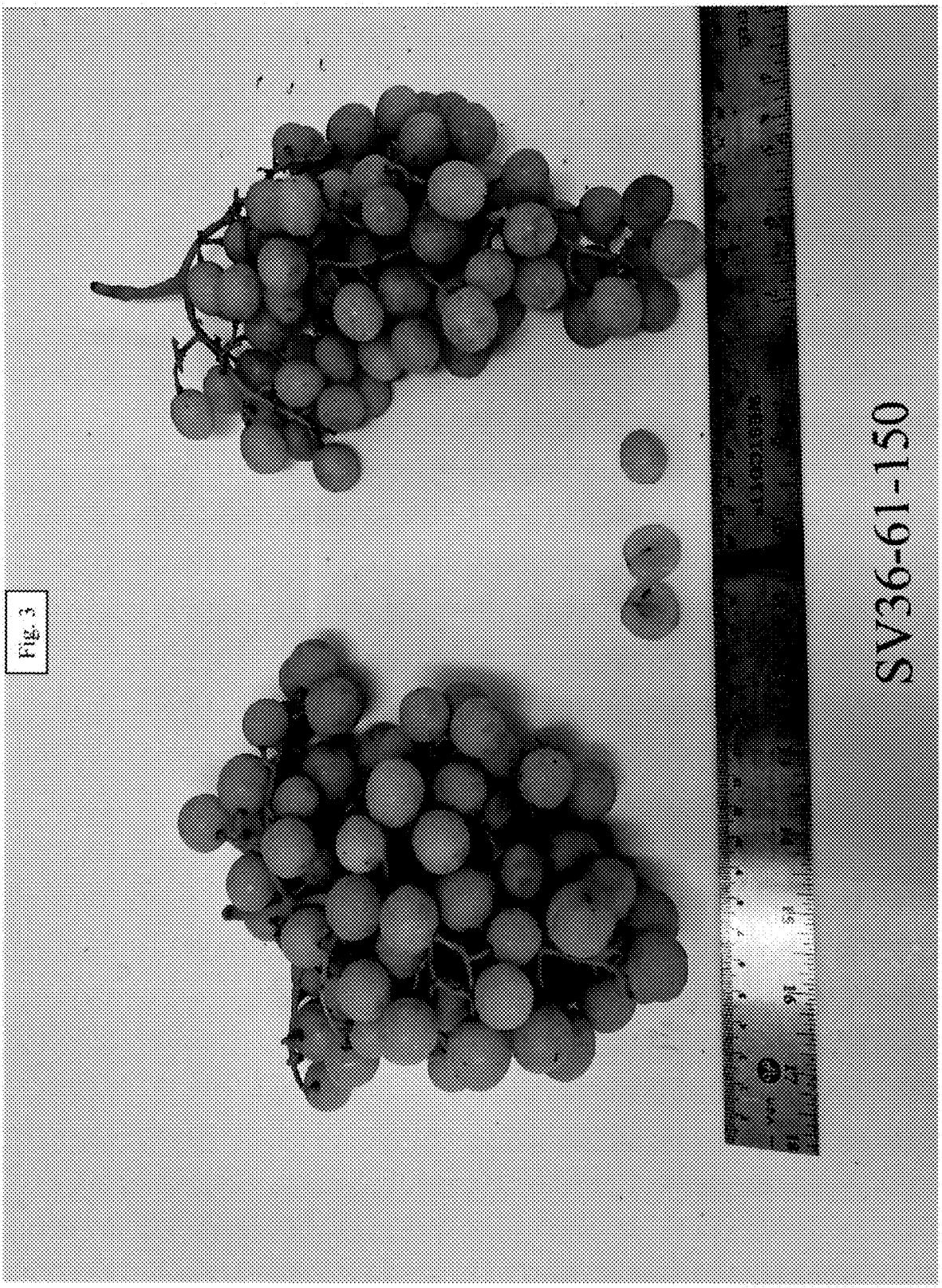
FIG. 3 Fruit cluster natural (at right) and fruit cluster treated with gibberellic acid and trunk girdling (at left) with green shoot bearing leaves and tendrils.
Figure 4:
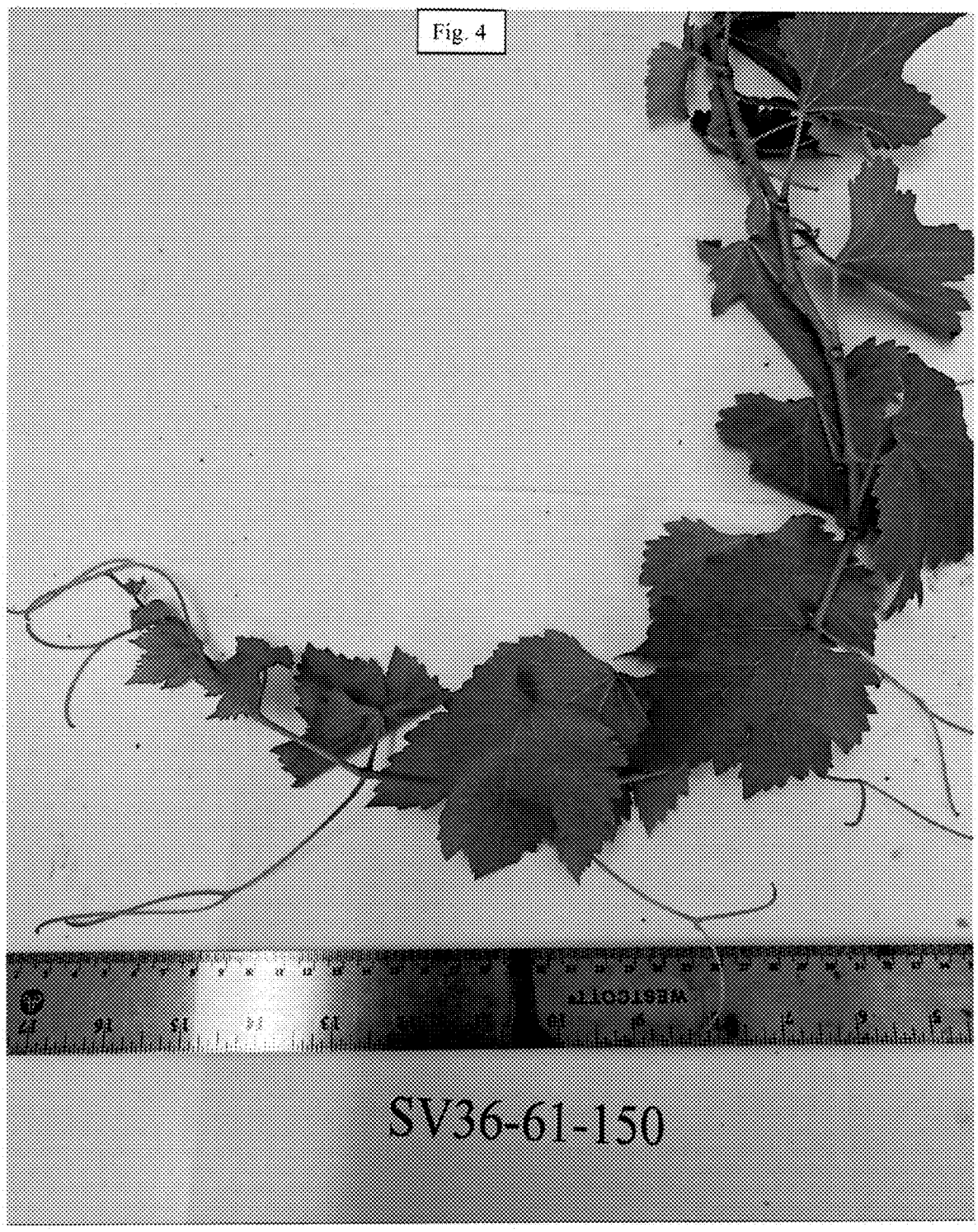
FIG. 4 Shoots, leaves and tendrils.
Figure 5:
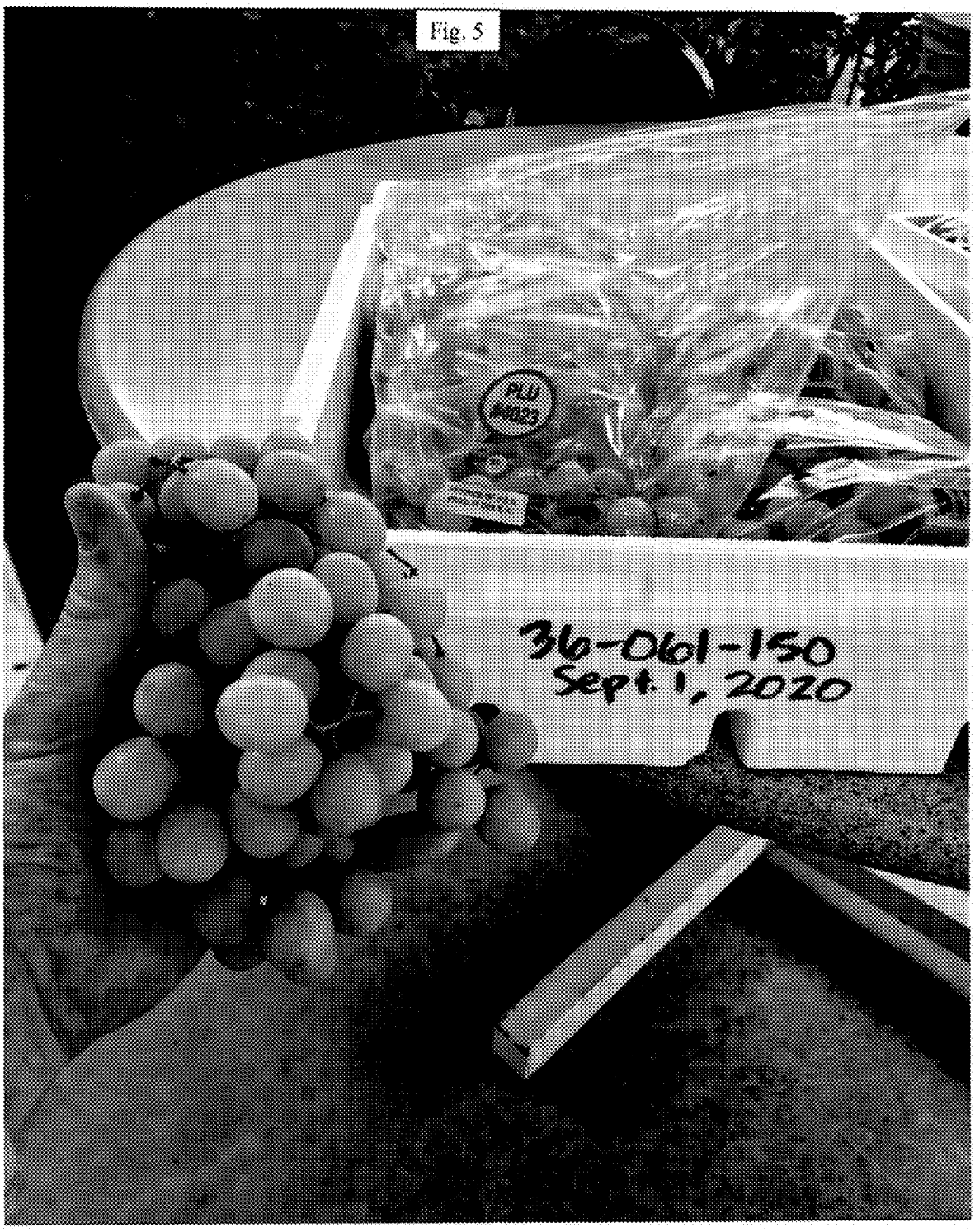
FIG. 5 Fruit clusters packaged for cold storage and shipping test.

The following detailed description sets forth the distinctive characteristics of grapevine named 'SV36-61-150'. Descriptions of the new invention apply to vines of grapevine named 'SV36-61-150' grown on 'Freedom' (unpatented) rootstock at a density of 1,537 vines per hectare grown near McFarland, California in 2022. These vines were in their fourth year of production having been planted in 2018. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV36-61-150'.

Plant:

*Vigor*.—Moderate.
*Density of foliage*.—Medium.
*Productivity*.—Moderate: 11,600 kg/hectare.
*Hardiness*.—Hardy to 0° centigrade.
*Rootstock*.—'Freedom' (unpatented).

Trunk:

*Shape*.—Broadly elliptical.
*Straps*.—Long, split.
*Surface texture*.—Shaggy.
*Trunk circumference*.—17.4 cm at 1.0 m of height.
*Inner bark color*.—RHS greyed-orange group 174B.
*Outer bark color*.—RHS grey group 201A.

Mature leaves:

*Average blade length*.—14.0 cm.
*Average blade width*.—17.0 cm.
*Size of blade*.—Medium.
*Number of lobes*.—5.
*Shape*.—Pentagonal.
*Anthocyanin coloration of main veins on the upper side of the blade*.—Present.
*Mature leaf profile*.—Cupping around entire margins.
*Blistering* (*upper surface*).—Absent.
*Leaf blade tip*.—Curved upwards.
*Margins*.—Lobed, serrate.
*Apex*.—Broadly acute.
*Base*.—Sagittate.
*Thickness*.—Medium.
*Undulation of blade between main and lateral veins*.—Slight.
*Shape of teeth*.—Both sides convex.
*Length of teeth*.—7.4 mm.
*Width of teeth*.—10.3 mm.
*Ratio length/width of teeth*.—7.4:10.3.
*General shape of petiole sinus*.—Half open.
*Tooth at petiole sinus*.—Absent.
*Petiole sinus limited by veins*.—Absent.
*Shape of upper lateral sinus*.—Slightly overlapping.
*Depth of upper lateral sinus*.—Medium.
*Prostrate hairs between veins* (*lower surface*).—Low density.
*Erect hairs between veins* (*lower surface*).—Medium density.
*Prostrate hairs on main veins* (*lower surface*).—Low density.
*Density of erect hairs on main veins* (*lower surface*).—Absent.
*Prostrate hairs on main veins* (*upper surface*).—Low density.
*Upper surface*.—Summer color: RHS yellow-green group 147A. Surface texture: Smooth. Surface appearance: Slightly glossy. Goffering of blade: Absent.
*Lower surface*.—Summer color: RHS yellow-green group 146A. Anthocyanin coloration of main veins on lower leaf surface: Present. Glossiness: Low. Pubescence distal portion of surface: Absent. Surface texture: Rough. Surface appearance: Dull.
*Petiole*.—Length: 11.4 cm. Length of petiole compared to middle vein: Slightly shorter. Density of prostrate hairs: Absent. Density of erect hairs: Absent. Shape of base of petiole sinus: Sagittate. Color: In shade: RHS greyed-orange group 166C. In sun: RHS greyed-orange group 166A.

Tendrils:

*Number*.—Bifurcated and trifurcated; forming continuous after 6th node.
*Length*.—26.3 cm.
*Diameter*.—4.4 mm.
*Texture*.—Smooth.
*Color*.—RHS yellow-green group 151A.

Growing tips:

*Color*.—RHS yellow-green group 144B.
*Anthocyanins*.—Absent.
*Shape*.—Rounded.
*Apex*.—Fully open.
*Prostrate hair on tips*.—Present.
*Anthocyanin coloration of prostrate hairs on tips*.—Absent.
*Erect hairs on tip*.—Absent.

Young shoots:

*Shoot attitude*.—Semi-erect.
*Color of dorsal side of internode*.—RHS greyed-orange group 166A.
*Color of ventral side of internode*.—RHS yellow-green group 144C.

*Color of dorsal side of nodes*.—RHS greyed-orange group 166A.

*Color of ventral side of nodes*.—RHS yellow-green group 144C.

*Erect hairs on internodes*.—Absent.

*Prostrate hairs on internodes*.—Absent.

Woody shoot:

*Canes*.—Shape: Broadly elliptical. Internode length: About 12.5 cm. Width at node: 16 mm. Surface: Smooth. Main color: RHS Greyed Orange group 166C. Lenticels: Inconspicuous.

*Laterals*.—Shape: Elliptical. Number: 1-2. Length: 22.0 cm. Diameter: 3.6 mm. Internode length: 4.3 cm. Color: RHS yellow-green group 145A.

*Buds*.—Shape: Slightly pointed. Cane bud fruitfulness: Basal buds fruitful, usually 2 clusters per shoot. Length: 6 mm. Width: 3.3 mm. Height: 3.7 mm. Color: RHS Greyed orange group 166B.

Flowers:

*Flower sex*.—Perfect.

*Position of first flowering nodes*.—4th or 5th node.

*Number of inflorescences per shoot*.—1 or 2.

*Flower cluster stem color*.—RHS yellow-green group 144B.

*Flower cluster width*.—5.8 cm.

*Flower cluster length*.—22.2 cm.

*Calyptra color*.—RHS yellow-green group 144A.

*Ovary length*.—1.5 mm.

*Ovary width*.—1 mm.

*Ovary color*.—RHS yellow-green group 143B.

*Filament length*.—1.6 mm.

*Filament color*.—RHS yellow-green group 145C.

*Anther length*.—0.7 mm.

*Anther color*.—RHS yellow group 8C.

*Date of full bloom*.—May 4, 2022 near McFarland, California.

Fruit:

*Ripening period*.—Early mid-season at McFarland, California.

*Date of ripening*.—Aug. 8, 2022 at McFarland, California.

*Use*.—Fresh market.

*Keeping quality*.—Very good.

*Shipping quality*.—Very good.

*Solids-sugar*.—22 brix at full maturity.

*Total acidity*.—0.77.

*pH*.—4.8.

*Bunch*.—Size: Medium. Length (peduncle excluded): 24.0 cm. Width: 19.5 cm. Weight: Natural, without gibberellic acid treatment: 995 g. With gibberellic acid treatment: 1105 g. Density: Well filled, medium density. Number of berries: Natural, without gibberellic acid treatment: 169. With gibberellic acid treatment: 177. Form: Long conical.

*Peduncle*.—Length: 7.0 cm. Lignification: 0.5 cm. Color: RHS yellow-green group 144C.

*Berry*.—Size: Medium. Uniformity of size: Uniform. Weight Natural, without gibberellic acid treatment: 5.77 g. With gibberellic acid treatment: 6.10 g. Shape: Natural, without gibberellic acid treatment: Spherical. With gibberellic acid treatment: Elliptic. Presence of seeds: Seedless; most berries develop one or two small, soft rudimentary seeds less than 1.0 mm in length. Cross section: Circular. Dimensions: Longitudinal axis (Control): 2.16 cm. Longitudinal axis (G & G): 2.37 cm. Horizontal axis (Control): 2.15 cm. Horizontal axis (G & G): 1.98 cm. Skin color (without bloom): RHS yellow-green group N144A. Coloration of flesh: RHS yellow-green group 145C. Juiciness of flesh: Very slightly juicy. Berry firmness: Very crisp. Particular flavor: Fruity, non-muscat. Bloom (cuticular wax): Medium. Pedicel length: 1.12 cm. Berry separation from pedicel: Slightly easy.

*Skin*.—Thickness: Medium. Texture: Crisp. Reticulation: Absent. Roughness: Absent. Tenacity: Tenacious to flesh. Tendency to crack: Resistant.

Disease and insect resistance: No particular resistance or susceptibility has been observed. Normal disease control practices can be used.

Having thus described and illustrated our new variety of grapevine, I claim:

1. A new and distinct variety of grapevine plant named 'SV36-61-150', substantially as illustrated and described herein.

* * * * *

96-150